United States Patent [19]
Huebner

[11] Patent Number: 6,001,099
[45] Date of Patent: Dec. 14, 1999

[54] BONE PLATE WITH VARYING RIGIDITY

[76] Inventor: Randall J. Huebner, 18650 SW. Hart Rd., Aloha, Oreg. 97007

[21] Appl. No.: 09/093,415

[22] Filed: Jun. 8, 1998

[51] Int. Cl.$^6$ .................................................... A61B 17/56
[52] U.S. Cl. ............................................................. 606/69
[58] Field of Search ................................ 606/69, 70, 71, 606/61, 60

[56] References Cited

U.S. PATENT DOCUMENTS

| | | | |
|---|---|---|---|
| 1,105,105 | 7/1914 | Sherman | 606/69 |
| 2,406,832 | 9/1946 | Hardinge . | |
| 2,443,363 | 6/1948 | Townsend et al. . | |
| 2,494,229 | 1/1950 | Collison | 606/69 |
| 4,364,382 | 12/1982 | Mennen . | |
| 4,565,193 | 1/1986 | Streli | 606/69 |
| 4,683,878 | 8/1987 | Carter . | |
| 4,955,886 | 9/1990 | Pawluk | 606/69 |
| 4,957,497 | 9/1990 | Hoogland et al. . | |
| 5,002,544 | 3/1991 | Klaue et al. . | |
| 5,015,248 | 5/1991 | Burstein et al. | 606/74 |
| 5,053,036 | 10/1991 | Perren et al. . | |
| 5,139,497 | 8/1992 | Tilghman et al. . | |
| 5,151,103 | 9/1992 | Tepic et al. . | |
| 5,190,544 | 3/1993 | Chapman et al. . | |
| 5,197,966 | 3/1993 | Sommerkamp | 606/69 |
| 5,201,737 | 4/1993 | Leibinger et al. . | |

(List continued on next page.)

FOREIGN PATENT DOCUMENTS 2367479  5/1978  France .

OTHER PUBLICATIONS

A comparison of Unicortical and Bicortical End Screw Attachment of Fracture Fixation Plates, Beaupre et al., *Journal of Orthopaedic Trauma*, vol. 6, No. 3, pp. 294–300, 1992.

Ace 4.5/5.0 mm Titanium Cannulated Screw an Reconstruction Plate System surgical technique brochure, Ace Medical Company, 1992.

Ace Titanium 3.5/4.0 mm Screw and Plate System with the Ace 3.5 mm Universal Ribbon description and parts list, Ace Medical Company, 1992.

Treatment of Three–and Four–Part Fractures of the Proximal Humerus with a Modified Cloverleaf Plate, Esser, *Journal of Orthopaedic Trauma*, vol. 8, No. 1, pp. 15–22, 1994.

The Ace Symmetry Titanium Upper Extremity Plates new product release, Ace Medical Company, 1996.

Ace Symmetry Titanium Upper Extremity Plates surgical technique brochure, Ace Medical Company, 1996.

Congruent Distal Radius Plate System description, Acumed, Inc., Mar. 4, 1998.

NexGen Osteotomy System (OS) surgical technique brochure, Zimmer, Inc., undated.

ECT Internal Fracture Fixation description, Zimmer, Inc., undated.

ECT Internal Fracture Fixation System order information, Zimmer, Inc., undated.

*Primary Examiner*—Michael Buiz
*Assistant Examiner*—Jonathan Goldberg
*Attorney, Agent, or Firm*—Kolisch, Hartwell, Dickinson, McCormack & Heuser

[57] ABSTRACT

An apparatus and method for securing a discontinuity in a bone. The apparatus generally comprises a bone plate with varying rigidity that includes a bridge portion configured to span the discontinuity and two anchor portions configured to contact the bone on opposite sides of the discontinuity. At least one anchor portion is an elongate structure having at least three apertures adapted to receive fasteners for affixing the elongate anchor portion to the bone. The minimum rigidity of the elongate anchor portion between the apertures second and third most distant from the bridge portion exceeds the minimum rigidity between the apertures first and second most distant from the bridge portion. In addition, the separation in the elongate anchor portion between the apertures first and second most distant from the bridge portion exceeds the separation between the apertures second and third most distant from the bridge portion. The method includes the step of securing a discontinuity in a bone using a bone plate with varying rigidity.

25 Claims, 1 Drawing Sheet

U.S. PATENT DOCUMENTS

| | | |
|---|---|---|
| 5,269,784 | 12/1993 | Mast . |
| 5,290,288 | 3/1994 | Vignaud et al. . |
| 5,304,180 | 4/1994 | Slocum ................................... 606/69 |
| 5,364,398 | 11/1994 | Chapman et al. ........................ 606/69 |
| 5,474,553 | 12/1995 | Baumgart . |
| 5,487,743 | 1/1996 | Laurain et al. . |
| 5,527,311 | 6/1996 | Proctor et al. ............................ 606/61 |
| 5,578,036 | 11/1996 | Stone et al. . |
| 5,647,872 | 7/1997 | Gilbert et al. ............................ 606/61 |
| 5,702,396 | 12/1997 | Hoenig et al. . |
| 5,709,686 | 1/1998 | Talos et al. . |
| 5,733,287 | 3/1998 | Tepic et al. . |
| 5,741,258 | 4/1998 | Klaue et al. . |
| 5,772,662 | 6/1998 | Chapman et al. . |

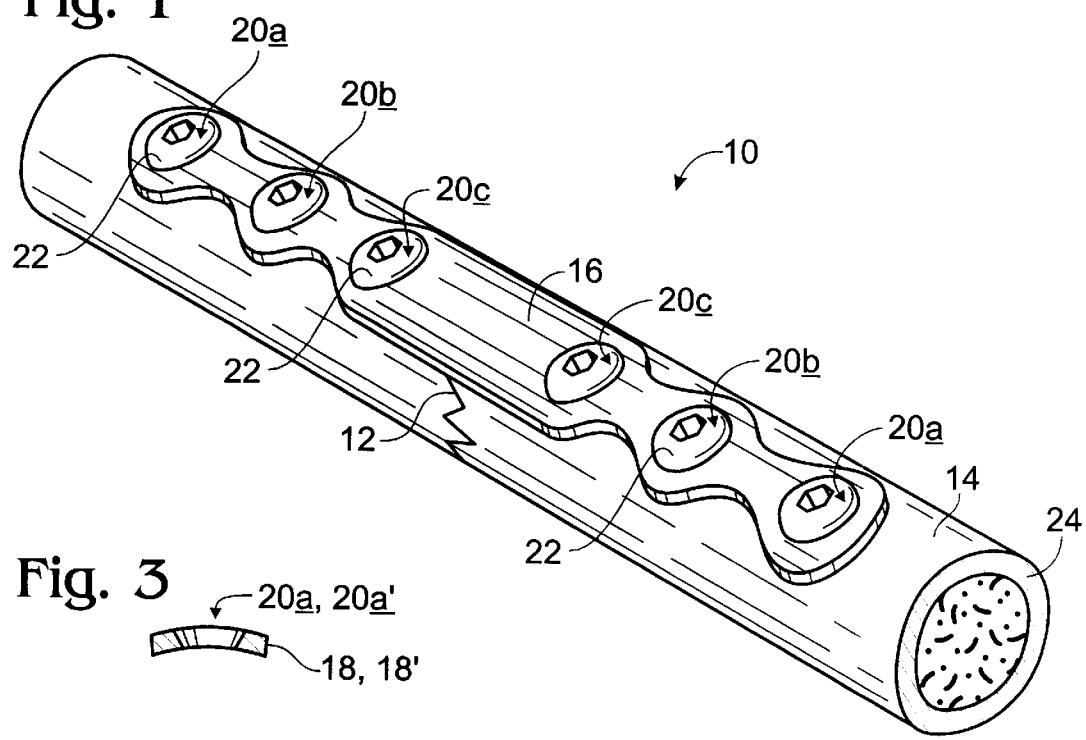
Fig. 1
Fig. 3
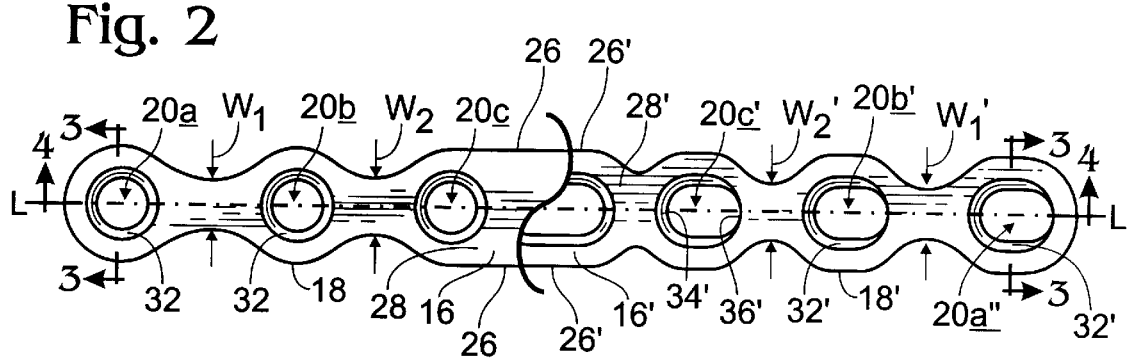
Fig. 2
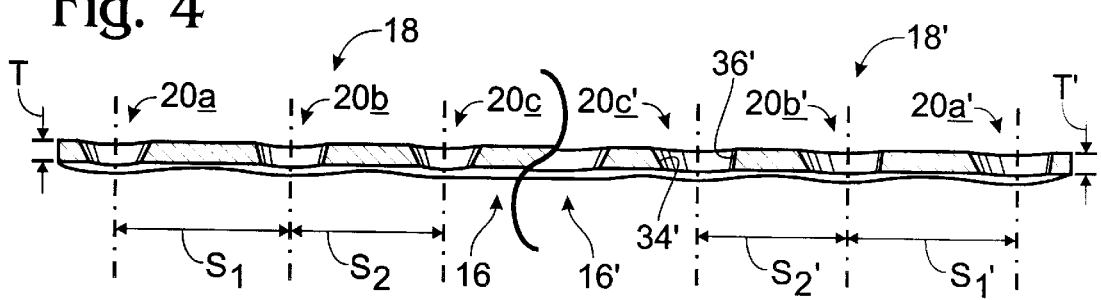
Fig. 4

BONE PLATE WITH VARYING RIGIDITY

TECHNICAL FIELD

The invention relates to bone plates. More particularly, the invention relates to bone plates with varying rigidity for securing a fracture or other discontinuity in a bone.

BACKGROUND OF THE INVENTION

Fractured bones often are treated using fixation devices, which reinforce the fractured bone and keep it aligned during healing. Fixation devices may take a variety of forms, including casts for external fixation and bone plates for internal fixation.

Bone plates probably are the most common internal fixation device and typically are formed as a rigid metal plate that is mounted on a fractured bone to span or bridge the fracture. Bone plates typically are held in place by screws or other fasteners attached to the bone on each side of the fracture through apertures in the bone plate.

Bone plates are considered the treatment of choice for many fractured bones, especially long bones, because they are compact, permitting an early return to motion. However, bone plates suffer from a number of shortcomings. In particular, bones reinforced by bone plates are subject to refracture near the ends of the bone plate. The rate of such refracture may be several percent, increasing medical costs and healing time and decreasing productivity.

Refractures associated with bone plates tend to occur through screw holes in the bone near the ends of the bone plate. In an attempt to reduce refracture, some clinicians attach bone plates less strongly at their ends, for example, by using unicortical screws. Unicortical screws penetrate through only half of the bone, so that the bone plate is held less securely, and the bone is not weakened by screw holes across its entire thickness. Unfortunately, the use of unicortical screws has provided mixed results, decreasing the rate of some kinds of refracture but increasing the rate of other kinds.

In another attempt to reduce refracture, some vendors have produced bone plates that are tapered toward their ends to reduce rigidity. Unfortunately, such tapering makes the bone plate narrower at its ends, creating focal points for stress transfer. Moreover, some tapered bone plates are designed to be attached to the bone by increased numbers of screws near the ends, weakening the bone plate and bone in the area prone to refracture.

SUMMARY OF THE INVENTION

The invention addresses these and other shortcomings by providing a bone plate with varying rigidity that gradually transfers load from the bone to the bone plate without excessively weakening the bone near the ends of the bone plate. The bone plate includes a bridge portion configured to span a discontinuity in the bone and two anchor portions extending outward from the bridge portion and configured to contact the bone on opposite sides of the discontinuity. At least one anchor portion is an elongate structure having at least three apertures adapted to receive fasteners for affixing the elongate anchor portion to the bone. In some embodiments, the minimum rigidity of the elongate anchor portion between the apertures second and third most distant from the bridge portion exceeds the minimum rigidity between the apertures first and second most distant from the bridge portion. In addition, the separation in the elongate anchor portion between the apertures first and second most distant from the bridge portion exceeds the separation between the apertures second and third most distant from the bridge portion.

The invention also provides a method of securing a discontinuity in a bone using a bone plate with varying rigidity.

The nature of the invention will be understood more fully by reference to the accompanying drawings and detailed description.

BRIEF DESCRIPTION OF THE DRAWINGS

FIG. 1 is a perspective view of a bone plate constructed in accordance with the invention; the bone plate is shown in use to secure a discontinuity in a bone.

FIG. 2 is a top plan view of portions of two alternative embodiments of a bone plate constructed in accordance with the invention.

FIG. 3 is a transverse cross-sectional view of the portions of bone plates in FIG. 2, taken generally along the lines 3—3 in FIG. 2.

FIG. 4 is a longitudinal cross-sectional view of the portions of bone plates in FIG. 2, taken generally along the line 4—4 in FIG. 2.

DETAILED DESCRIPTION

FIG. 1 shows a bone plate 10 constructed in accordance with the invention. Bone plate 10 is used to secure a discontinuity 12 in a bone 14. Bone plate 10 may be used to secure various discontinuities, including breaks, fractures, and excisions, at various positions in various bones. Bone plates constructed according to the invention, such as bone plate 10, are particularly adapted to secure mid-shaft discontinuities in long bones, such as the femur, fibula, humerus, metacarpals, radius, tibula, and ulna, among others.

Bone plate 10 includes a bridge portion 16 configured to span discontinuity 12 in bone 14 and two elongate anchor portions 18 extending outward from bridge portion 16 and configured to contact bone 14 on opposite sides of discontinuity 12. Together, bridge portion 16 and anchor portions 18 form a unitary structure with a curvature that substantially matches the curvature of bone 14.

Anchor portions 18 have apertures 20a–c adapted to receive fasteners 22 for affixing the anchor portions to a cortex 24 of bone 14. As further described below, the minimum rigidity of anchor portions 18 between apertures 20b,c second and third most distant from bridge portion 16 exceeds the minimum rigidity of anchor portions 18 between apertures 20a,b first and second most distant from bridge portion 16, and the separation between apertures 20a,b first and second most distant from bridge portion 16 exceeds the separation between apertures 20b,c second and third most distant from bridge portion 16.

Generally, bone plate 10 is configured to minimize irritation to the bone and surrounding tissue. For example, bone plate 10 is formed of a bio-compatible material, such as titanium or stainless steel. In addition, bone plate 10 has a low profile that minimizes its protrusion into adjacent tissue and rounded, burr-free surfaces that minimize the effects of such protrusion.

Bone plate 10 is substantially symmetric about an axis through bridge portion 16, making it suitable for fixing mid-shaft fractures. Other bone plates constructed in accordance with the invention may be asymmetric, so long as at least one anchor portion is elongate with at least three apertures.

Bone plate 10 may be used as follows. Discontinuity 12 in bone 14 is reduced by appropriate means, such as manually. Bone plate 10 is positioned through a surgical incision, so that bridge portion 16 spans discontinuity 12 and anchor portions 18 contact reduced bone 14 on opposite sides of discontinuity 12. Bone plate 10 may be preformed to mate with bone 14, or it may be bent to mate during fixation. Holes are drilled in bone 14, and bone plate 10 is secured to bone 14 by passing fasteners 22 through the holes and through apertures 20*a,c*. After bone 14 is sufficiently healed, bone plate 10 and fasteners 22 may be removed. Patients with broken bones may be anesthetized during reduction, fixation, and removal to minimize discomfort.

FIGS. 2–4 show portions of alternative embodiments of bone plates 10, 10' constructed in accordance with the invention. Bone plates 10, 10' are formed of a biocompatible material and include a bridge portion 16, 16' and an anchor portion 18, 18'.

Bridge portions 16, 16' are configured to span a discontinuity in a bone. Bridge portions 16, 16' are substantially rectangular, with opposed sides 26, 26' and ends 28, 28' and a cylindrical curvature to mate with a bone. Bridge portions 16, 16' have a substantially uniform thickness T, T' along a direction perpendicular to the direction of curvature and a substantially uniform width W, W' along a direction parallel to the direction of curvature. Alternative bridge portions may have other shapes. Bridge portion 16 has no apertures. Bridge portion 16' has one aperture 30, which alters its rigidity and facilitates blood flow to the fracture to promote healing. Alternative bridge portions may have two or more apertures.

Anchor portions 18, 18' are configured to contact the bone on opposite sides of the discontinuity. Anchor portions 18, 18' are elongate structures that extend outward from opposed ends 28, 28' of bridge portions 16, 16' to define long axes L, L'. Anchor portions 18, 18' also have a cylindrical curvature to mate with a bone. Anchor portions 18, 18' have a substantially uniform thickness T, T' along a direction perpendicular to the direction of curvature and to long axes L, L' and a substantially varying width W, W' along a direction parallel to the direction of curvature.

Anchor portions 18, 18' have three substantially colinear apertures 20*a–c*, 20*a'–c'* adapted to receive fasteners for affixing the anchor portions to the bone. Alternative anchor portions may have four or more apertures, or noncolinear apertures. Widths W, W' of anchor portions 18, 18' vary such that they are substantially the same at bridge portions 16, 16' and at each aperture 20*a–c*, 20*a'–c'*. The width of bone plate 10 is a maximum where bridge portion 16 and anchor portion 18 abut. The width of bone plate 10' is a local minimum where bridge portion 16' and anchor portion 18' abut.

A preferred fastener for use with apertures 20*a–c*, 20*a'–c'* is a bone screw, such as a unicortical or bicortical bone screw. Unicortical bone screws penetrate the bone cortex once, adjacent the bone plate. Bicortical bone screws penetrate the bone cortex twice, adjacent the bone plate and opposite the bone plate. Generally, unicortical screws provide less support than bicortical screws, because they penetrate less cortex. Different-width fasteners may be accommodated with different-width apertures.

Apertures may have a variety of geometries. In bone plate 10, apertures 20*a–c* are substantially circular. In bone plate 10', apertures 20*a'–c'* are substantially oval. In both bone plates, apertures 20*a–c*, 20*a'–c'* contain counterbores 32, 32' that permit fasteners to lie substantially flush with the top surface of the bone plates. Apertures 20*a'–c'* contain a tapered counterbore 32' for biasing a fastener away from bridge portion 16'. In particular, apertures 20*a'–c'* contain a sloping wall 34' that biases fasteners toward a vertical wall 36' away from bridge portion 16'. Alternative apertures may contain a tapered counterbore for biasing a fastener toward bridge portion 16'.

The minimum rigidity of anchor portions 18, 18' between apertures 20*b,c*, 20*b',c'* second and third most distant from bridge portion 16, 16' exceeds the minimum rigidity of anchor portions 18, 18' between apertures 20*a,b*, 20*a',b'* first and second most distant from bridge portion 16, 16'. The rigidity of anchor portions 18, 18' is varied in part by varying the cross-sectional area of the anchor portions perpendicular to long axes L, L'. Specifically, the cross-sectional area is the product of width W, W' and thickness T, T' of anchor portions 18, 18'. In bone plates 10, 10', thickness T, T' is constant, and width W, W' varies. The minimum width $W_1$, $W_1'$ and hence rigidity between apertures 20*b,c*, 20*b',c'* second and third most distant from bridge portion 16, 16' exceeds the minimum width $W_2$, $W_2'$ and hence rigidity of anchor portions 18, 18' between apertures 20*a,b*, 20*a',b'* first and second most distant from bridge portion 16, 16'. The minimum cross-section may occur at points substantially midway between apertures. The rigidity of anchor portions 18, 18' also may be varied in part by varying the rigidity of the material comprising the anchor portions, for example, by varying the annealing of the bone plate as a function of position during manufacture. In anchor portions containing more than three apertures, the minimum rigidity between adjacent apertures may decrease as the distance of the apertures from the bridge portion increases for the three apertures most distant from the bridge portion or for those and additional apertures. This effect is shown in FIGS. 2 and 4, if aperture 30' in bridge portion 16' is taken to lie in anchor portion 18'.

The separation $S_1$, $S_1'$ in anchor portions 18, 18' between apertures 20*a,b* first and second most distant from the bridge portion exceeds the separation $S_2$, $S_2'$ between apertures 20*b,c* second and third most distant from the bridge portion. In anchor portions having more than three apertures, the separation between adjacent apertures may increase as the distance of the apertures from the bridge portion increases for the three apertures most distant from the bridge portion or for those and additional apertures. This effect is shown in FIGS. 2 and 4, if aperture 30' in bridge portion 16' is taken to lie in anchor portion 18'.

Both the decrease in intra-aperture rigidity and the increase in intra-aperture spacing in the invention reduce the likelihood of refracture. Load is transferred relatively gradually from the bone to the bone plate, rather than abruptly near the ends of the bone plate. Because the spacing between apertures increases toward the ends of the bone plate, the bone is not excessively weakened near the ends of the bone plate by an increased density of screw holes. Moreover, because the minimum rigidity of the bone plate is shifted to positions between apertures, the weakest point of the bone plate is not aligned with the weakest points of the bone (the screw holes).

The invention also provides a method of securing a discontinuity in a bone. The method includes (a) providing a bone plate with varying rigidity, (b) reducing the discontinuity, and (c) affixing the bone plate to the bone so that the two anchor portions contact the bone on opposite sides of the discontinuity and the bridge portion spans the discontinuity. The bone plate with varying rigidity used in the method includes a bridge portion configured to span the discontinuity in the bone and two anchor portions extending outward from the bridge portion and configured to contact the bone on opposite sides of the discontinuity. At least one anchor portion is an elongate structure having at least three apertures adapted to receive fasteners for affixing the elongate anchor portion to the bone. The minimum rigidity of the elongate anchor portion between the apertures second and third most distant from the bridge portion exceeds the minimum rigidity of the anchor portion between the apertures first and second most distant from the bridge portion. In addition, the separation in the elongate anchor portion between the apertures first and second most distant from the bridge portion exceeds the separation between the apertures second and third most distant from the bridge portion.

While the invention has been disclosed in its preferred form, the specific embodiment thereof as disclosed and illustrated herein is not to be considered in a limiting sense as numerous variations are possible and no single feature, function or property of the preferred embodiment is essential. The invention is to be defined only by the scope of the issued claims.

I claim:

1. An elongate bone plate with varying rigidity for securing a discontinuity in a bone, the bone plate being formed of a bio-compatible material and comprising:
    a bridge portion configured to span the discontinuity in the bone; and
    two anchor portions extending outward from the bridge portion and configured to contact the bone on opposite sides of the discontinuity, at least one anchor portion being an elongate structure having at least three apertures adapted to receive fasteners for affixing the elongate anchor portion to the bone;
    wherein in the elongate anchor portion the width of the anchor portion about the apertures first and second most distant from the bridge portion exceeds the minimum width of the anchor portion between such apertures;
    wherein in the elongate anchor portion the minimum rigidity of the anchor portion between the apertures second and third most distant from the bridge portion exceeds the minimum rigidity of the anchor portion between the apertures first and second most distant from the bridge portion; and
    wherein in the elongate anchor portion the separation between the apertures first and second most distant from the bridge portion exceeds the separation between the apertures second and third most distant from the bridge portion.

2. The bone plate of claim 1, wherein the apertures in the elongate anchor portion are substantially colinear.

3. The bone plate of claim 1, wherein the bone plate is of substantially uniform thickness.

4. The bone plate of claim 3, wherein the apertures in the elongate anchor portion are substantially colinear.

5. The bone plate of claim 1, wherein the cross-sectional area of the elongate anchor portion perpendicular to an axis connecting pairs of apertures is varied to vary the rigidity of the anchor portion.

6. The bone plate of claim 1, wherein the rigidity of the material comprising the elongate anchor portion is varied to vary the rigidity of the anchor portion.

7. The bone plate of claim 1, wherein the rigidity of the elongate anchor portion is substantially the same about each aperture.

8. The bone plate of claim 1, wherein the separation between adjacent apertures in the elongate anchor portion increases as the distance of the apertures from the bridge portion increases.

9. The bone plate of claim 1, wherein the minimum rigidity between adjacent apertures in the elongate anchor portion decreases as the distance of the apertures from the bridge portion increases.

10. The bone plate of claim 9, wherein the separation between each such pair of adjacent apertures increases as the distance of such pairs from the bridge portion increases.

11. An elongate bone plate with varying rigidity for securing a mid-shaft discontinuity in a bone, the bone plate being formed of a bio-compatible material and comprising:
    a bridge portion configured to span the mid-shaft discontinuity in the bone, the bridge portion having opposed ends; and
    two oppositely directed anchor portions extending outward from the opposed ends of the bridge portion to define a long axis and configured to contact the bone on opposite sides of the discontinuity, each anchor portion having, at each point along the long axis, a cross-sectional area transverse to the long axis, and each anchor portion having at least three apertures adapted to receive fasteners for affixing the elongate anchor portion to the bone;
    wherein in each anchor portion the minimum cross-sectional area between the apertures second and third most distant from the bridge portion exceeds the minimum cross-sectional area between the apertures first and second most distant from the bridge portion; and
    wherein in each anchor portion the separation between the apertures first and second most distant from the bridge portion exceeds the separation between the apertures second and third most distant from the bridge portion.

12. The bone plate of claim 11, wherein the bone plate is of substantially uniform thickness.

13. The bone plate of claim 11, wherein the bone plate is symmetric about at least one axis.

14. The bone plate of claim 13, wherein each anchor portion has three apertures.

15. The bone plate of claim 14, wherein the minimum cross-sectional area occurs at a point substantially midway between such apertures.

16. The bone plate of claim 11, wherein the apertures in at least one anchor portion are substantially colinear.

17. The bone plate of claim 11, wherein the separation between adjacent apertures in at least one anchor portion increases as the distance of the apertures from the bridge portion increases.

18. The bone plate of claim 11, wherein the minimum cross-sectional area of the anchor portion between each pair of adjacent apertures decreases as the distance of such pairs from the bridge portion increases.

19. The bone plate of claim 18, wherein the separation between each such pair of adjacent apertures increases as the distance of such pairs from the bridge portion increases.

20. A method of securing a discontinuity in a bone, the method comprising:
    (a) providing a bone plate with varying rigidity, the bone plate including:
        a bridge portion configured to span the discontinuity in the bone; and
        two anchor portions extending outward from the bridge portion and configured to contact the bone on opposite sides of the discontinuity, at least one anchor portion being an elongate structure having at least three apertures adapted to receive fasteners for affixing the elongate anchor portion to the bone;

wherein in the elongate anchor portion the width of the anchor portion about the apertures first and second most distant from the bridge portion exceeds the minimum width of the anchor portion between such apertures;

wherein in the elongate anchor portion the minimum rigidity of the anchor portion between the apertures second and third most distant from the bridge portion exceeds the minimum rigidity of the anchor portion between the apertures first and second most distant from the bridge portion; and wherein in the elongate anchor portion the separation between the apertures first and second most distant from the bridge portion exceeds the separation between the apertures second and third most distant from the bridge portion (b) reducing the discontinuity; and (c) affixing the bone plate to the bone so that the two anchor portions contact the bone on opposite sides of the discontinuity and the bridge portion spans the discontinuity.

21. The bone plate of claim 1, wherein in the elongate anchor portion the width of the anchor portion about the apertures second and third most distant from the bridge portion exceeds the minimum width of the anchor portion between such apertures.

22. The bone plate of claim 21, wherein in the elongate anchor portion the minimum width of the anchor portion between the apertures second and third most distant from the bridge portion exceeds the minimum width of the anchor portion between the apertures first and second most distant from the bridge portion.

23. The bone plate of claim 1, wherein the width of at least a portion of the elongate anchor portion undulates, the width of the anchor portion being a local maximum about the apertures first, second, and third most distant from the bridge portion, the width of the anchor portion being a local minimum between adjacent pairs of such apertures.

24. An elongate bone plate with varying rigidity for securing a discontinuity in a bone, the bone plate being formed of a bio-compatible material and comprising:

a bridge portion configured to span the discontinuity in the bone; and two anchor portions extending outward from the bridge portion and configured to contact the bone on opposite sides of the discontinuity, at least one anchor portion being an elongate structure having at least three apertures adapted to receive fasteners for affixing the elongate anchor portion to the bone;

wherein in the elongate anchor portion the rigidity of the material comprising the anchor portion is varied to vary the rigidity of the anchor portion;

wherein in the elongate anchor portion the minimum rigidity of the anchor portion between the apertures second and third most distant from the bridge portion exceeds the minimum rigidity of the anchor portion between the apertures first and second most distant from the bridge portion; and wherein in the elongate anchor portion the separation between the apertures first and second most distant from the bridge portion exceeds the separation between the apertures second and third most distant from the bridge portion.

25. An elongate bone plate with varying rigidity for securing a discontinuity in a bone, the bone plate being formed of a bio-compatible material and comprising:

a bridge portion configured to span the discontinuity in the bone; and two anchor portions extending outward from the bridge portion and configured to contact the bone on opposite sides of the discontinuity, at least one anchor portion being an elongate structure having at least three apertures adapted to receive fasteners for affixing the elongate anchor portion to the bone;

wherein in the elongate anchor portion the rigidity of the anchor portion about each aperture is substantially the same, and the minimum rigidity of the anchor portion between the apertures second and third most distant from the bridge portion exceeds the minimum rigidity of the anchor portion between the apertures first and second most distant from the bridge portion; and wherein in the elongate anchor portion the separation between the apertures first and second most distant from the bridge portion exceeds the separation between the apertures second and third most distant from the bridge portion.

* * * * *